United States Patent
Kuoni et al.

(10) Patent No.: US 7,018,417 B2
(45) Date of Patent: Mar. 28, 2006

(54) ARTIFICIAL SOCKET

(76) Inventors: Xaver Kuoni, Alter Zürichweg 33, Schlieren (CH) CH-8952; Hannes Hofer, Dossenweg 26, Salzburg (AT) A-5020

( * ) Notice: Subject to any disclaimer, the term of this patent is extended or adjusted under 35 U.S.C. 154(b) by 0 days.

(21) Appl. No.: 10/485,880

(22) PCT Filed: Jul. 31, 2001

(86) PCT No.: PCT/CH01/00466

§ 371 (c)(1),
(2), (4) Date: Feb. 2, 2004

(87) PCT Pub. No.: WO03/011196

PCT Pub. Date: Feb. 13, 2003

(65) Prior Publication Data

US 2004/0243247 A1    Dec. 2, 2004

(51) Int. Cl.
*A61F 2/34* (2006.01)
(52) U.S. Cl. .............................. 623/22.32; 623/22.23; 623/22.38
(58) Field of Classification Search ............ 623/22.21, 623/22.23, 22.27, 22.31, 22.32, 22.38
See application file for complete search history.

(56) References Cited

U.S. PATENT DOCUMENTS

| | | | |
|---|---|---|---|
| 3,840,904 A | | 10/1974 | Tronzo |
| 4,743,262 A | * | 5/1988 | Tronzo ............... 623/22.32 |
| 6,537,321 B1 | * | 3/2003 | Horber ............... 623/22.22 |

FOREIGN PATENT DOCUMENTS

| | | |
|---|---|---|
| EP | 0 923 915 A2 | 11/1998 |
| EP | 1 068 843 A1 | 4/2000 |
| EP | 1 099 426 A1 | 11/2000 |
| EP | 1 072 236 A1 | 6/2001 |
| FR | 2 716 106 A1 | 2/1994 |
| WO | WO 99/03429 | 1/1999 |

* cited by examiner

*Primary Examiner*—David J. Isabella
(74) *Attorney, Agent, or Firm*—Janet Sleath; Victor N. King; Speckman Law Group PLLC

(57) ABSTRACT

The present invention relates to a socket for an artificial hip joint. The present invention provides an artificial joint socket for knocking into a bone, with an excellent primary stabilization, which may be manufactured so that at least two locking elements are arranged in the distal superficies region of the socket shell. The locking elements anchor the socket shell in the hip bone and safeguard against tensile forces, torsion forces, and combined tensile and torsion forces. The locking elements effectively prevent the socket from rotating-out opposite the knock-in direction. When knocking in the implant, the locking elements cut into the bone and rotate the socket shell about the socket axis by a few degrees. The socket of the present invention forms a gradient of web-like locking elements with respect to the socket base surface, increasing from the distal or equatorial end towards the proximal or pole-side end, enabling the locking elements to jam and lock the implant against axial tensile forces, radial torsion forces, as well as the combination of both forces.

20 Claims, 7 Drawing Sheets

ARTIFICIAL SOCKET

FIELD OF INVENTION

The present invention relates generally to an artificial joint socket.

BACKGROUND OF THE INVENTION

An artificial hip joint usually comprises a joint socket provided with an insert into which the head of a shank engages. Analogous to the natural joint to be replaced, the artificial joint socket must be mounted in the socket of the pelvic bone of the patient in a positionally accurate and stable manner. Various artificial hip sockets are known, with two types of socket being most commonly used: conically shaped sockets and spherical sockets. The decision to use one or the other socket type is dependant on the medical condition and the preference of the operating physician.

Both socket types comprise a metallic outer shell, an insert, and an inlay arranged in the outer shell. The inlay is usually made of ceramic, plastics, such as polyethylene (chirulene), or metal. Such an artificial joint socket, having a shell and an insert, has been shown to be very reliable.

One advantage of using the spherical sockets is that during pre-milling of the spherical bed, less pelvic bone needs to be removed than with a conically-shaped socket, since the acetabulum is approximately spherical even with greatly deformed joints. The milling process is also easier with spherical sockets than with conical sockets since milling does not need to be so accurate. Further, the danger of the ileum, ischium or pubis becoming damaged due to milling too deep is much lower with a spherical bed than with a conical one.

In addition to the standard design of a spherical socket which corresponds to a hemisphere, press-fit designs have also been successfully applied. The press-fit sockets are slightly flattened at the pole and are somewhat larger in diameter than the pre-milled hemispherical bed in the bone. The force-fit of the socket in the pre-milled bone is thus ensured. A rough surface coating is provided on shells made of metals, such as pure titanium, to permit the intergrowth of the bone cells onto the implant, ensuring an optimal secondary stabilization in the long term. One may also fill behind the press-fit socket with spongiosa in order to achieve an improved retention on the bone. The primary stability of a press-fit socket is usually increased by several additional spongiosa screws or other fixation means. As described in EP-B-0,601,224 and EP-A-0,943,304, the primary stability of a screw socket is increased by way of self-cutting threads which run around the outside of the socket base body.

In contrast to screw sockets, spherical sockets without threads, and press-fit sockets are pressed into the pre-milled bed in a linear movement.

Standardized socket sizes of 44 to 66, i.e. sockets with a diameter of 44 to 66 mm on the socket base surface, are common and readily available on the market.

Various devices have been designed in order to achieve an improved primary stability with these socket types. An artificial joint socket with a basal flange is described in U.S. Pat. No. 4,173,797 in the year 1979, in which, in the inserted condition, the socket bears on the surface of the bone and as a result, prevents tilting of the outer shell. Additional barbs in the pole region of the convex outer side of the shell are also described. The barbs act as rotational sacraments before the implant grows in. U.S. Pat. No. 5,972,032 describes another type of spherical implant having barb-like projections, or spikes, in the pole region. The press-fit socket shown in this reference is knocked in essentially along the longitudinal or rotation axis of the shell body, and the socket is fixed in a rotationally secure manner in the knocked-in condition by way of the spikes, which are arranged essentially parallel to the longitudinal or rotation axis of the implant in the pole region. These spikes, however, only slightly contribute to safeguarding against tensile loads. It is known that compressive forces with a significant axial component in the femur may be built up with press-fit sockets. Moreover, the above described spikes may not primarily safeguard against these forces. Two additional solutions to the problem of insufficient primary securement are described in U.S. Pat. No. 5,755,799 and U.S. Pat. No. 6,231,612. In order to permit a screwless and cementless fixation in the bed of the bone, both implants in the equatorial region of the outer side of the shell comprise a multitude of small projections. The tips of these scale-like or tile-like barbs point distally with respect to the body of the patient, and are thus counter to the knock-in direction. On account of manufacturing technology, the tips follow the contour of the superficies exactly, and the individual rows of scales run from the shell opening in the direction of the pole parallel to the knock-in direction. The manufacture of such implants is very complicated and is thus very expensive. In addition, the barbs are only a few tenths of a millimeter high, and often do not provide the freshly inserted implant with the required amount of primary stability.

SUMMARY OF THE INVENTION

It is therefore the object of the present invention to provide an artificial joint socket which does not have the above-mentioned disadvantages and ensures a particularly simple and exact implantation and a reliable primary fixation. Another object of the invention is to provide optimal recovery of the anatomical function of the socket of the hip joint with a physiological introduction of force.

The present invention provides an artificial joint socket for knocking into a pre-milled bed in the bone, with an excellent primary stabilization, in which at least two locking elements are arranged in the distal superficies region of the socket shell. The inventive locking elements anchor the socket shell in the hip bone and safeguard against tensile forces, torsion forces, and combined tensile and torsion forces. The inventive locking elements at first appear similar to known webs formed of a coarse thread. However the geometry of the inventive locking elements deviates from that of common thread webs so that they effectively prevent the socket from rotating-out opposite the knock-in direction. On knocking in the implant, the locking elements cut into the bone and rotate the socket shell about the socket axis by a few degrees. In a preferred embodiment, the gradient of the web-like locking elements with respect to the socket base surface, increases from the distal, or equatorial, end towards the proximal, or pole-side end, thereby enabling the locking elements to jam and lock the implant against axial tensile forces, radial torsion forces, as well as combinations of both forces.

BRIEF DESCRIPTION OF THE DRAWINGS

Further advantages and embodiments of the present invention are explained in the following description with reference to the attached drawings, wherein.

DETAILED DESCRIPTION OF THE INVENTION

Figure 1A:
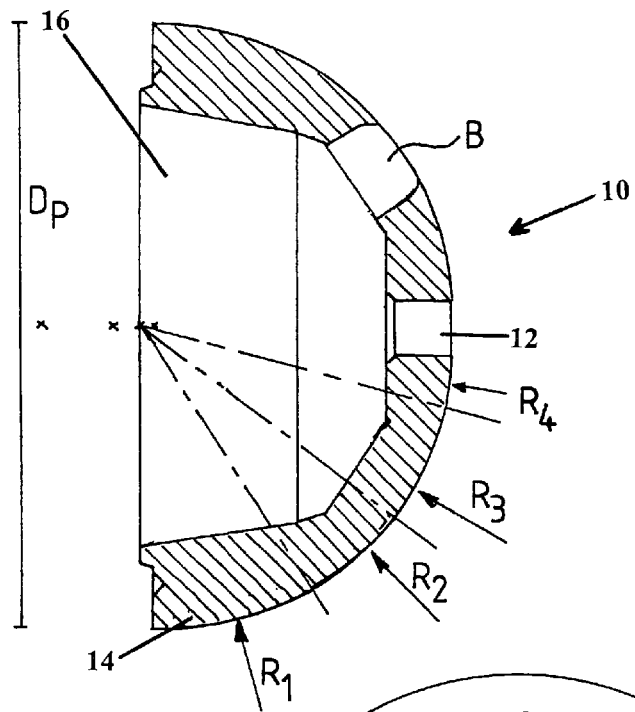
FIG. 1a shows a cross-sectional view of a press-fit socket known in the art, wherein only a shell is shown and the inlay is omitted.

FIG. 1a shows a cross-sectional view of a base body or shell 10 of a press-fit socket according to known in the art. This type of press-fit socket deviates from the hemispherical shape by its increased flattening in the direction of the pole region 12. The base body 10, as indicated by the dashed lines, may be divided into four socket layers. The associated superficies in each layer have a radius $R_1$, $R_2$, $R_3$, $R_4$ which increases from the distal end 14, i.e. distant to the pole, to the proximal end. The shown sectional plane contains the axis of the socket. The inside of the shell 10 comprises a recess 16 for accommodating a ceramic or plastic inlay. This inlay, not shown in the figure, serves as a counter bearing for the ball head of a femoral prosthesis, also referred to as a shank.

Figure 1B:
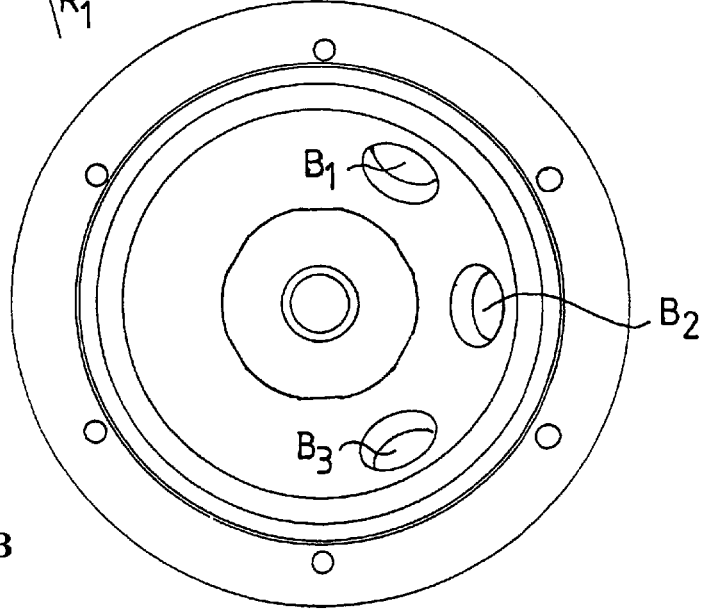
FIG. 1b shows a top view of the socket of FIG. 1a, illustrating the inside of the shell.

The socket according to the present invention has all the essential advantages of the known press-fit socket shown in FIG. 1a, with regard to material selection, surface coatings and socket geometry. One element of the known socket which has been omitted from the socket of the present invention is the bores $B_1$, $B_2$ and $B_3$, shown in FIG. 1b. The bores $B_1$, $B_2$, $B_3$ accommodate spongiosa screws, which provide additional primary stabilization of the implant in the bone.

Figure 2:
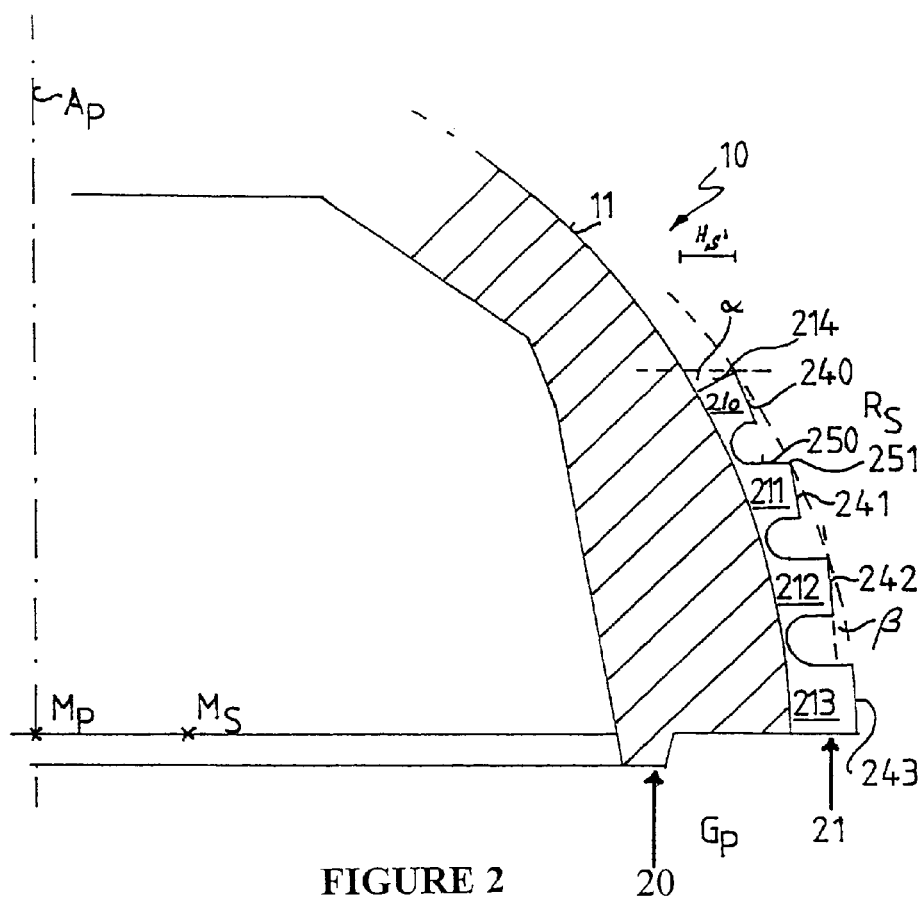
FIG. 2 shows a partial cross-sectional view of the press-fit socket according to the present invention, in the region of a locking element, wherein only the shell is shown and the inlay has been omitted.

FIG. 2 shows a half cross-sectional view of a socket 1, designed for an artificial hip joint. A socket axis $A_p$ lies in the section plane. A base body or a shell 10 is provided with a spherical or ellipsoidal superficies, or outer surface 11, which is essentially rotationally symmetrical to the socket axis $A_p$. At least two locking elements 20 are provided on the outer side of the base body 10. In FIG. 2, only one of the at least two locking elements 20 is shown. The locking element 20 comprises a knock-in web 21 which in the embodiment of FIG. 2, is toothed.

The locking elements 20 are distributed symmetrically over the periphery of the socket 1 so that the resulting forces from the socket 1 being knocked-in are uniformly distributed and thus the socket does not tilt. In a preferred embodiment, the locking elements 20 are arranged uniformly distanced to one another. If three locking elements 20 are provided, the elements 20 are arranged in the positions at 0°, 120°, and 240° with respect to a circular socket base surface $G_P$. If four elements 20 are provided, the elements 20 are arranged in the positions at 0°, 90°, 180°, and 270° with respect to a circular socket base surface $G_P$. The elements 20 may also be distanced irregularly from one another as long as the symmetry is retained, such that four elements may be arranged in the following positions: 0°, 60°, and 180°, and 240°.

Figure 3:
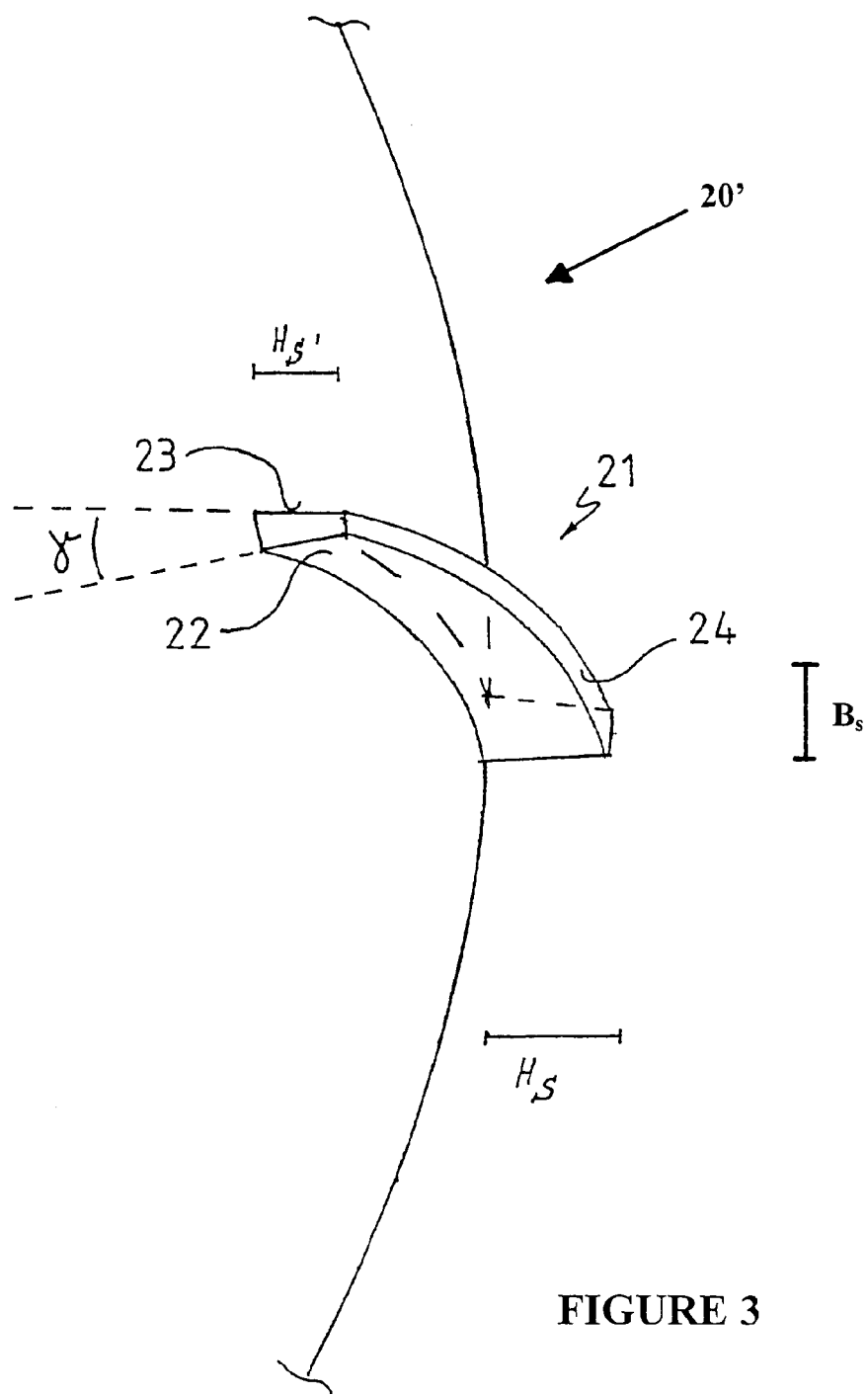
FIG. 3 shows a partial view of a locking element of another embodiment of the joint socket of the present invention, viewed from the proximal end or from the pole.
Figure 4:
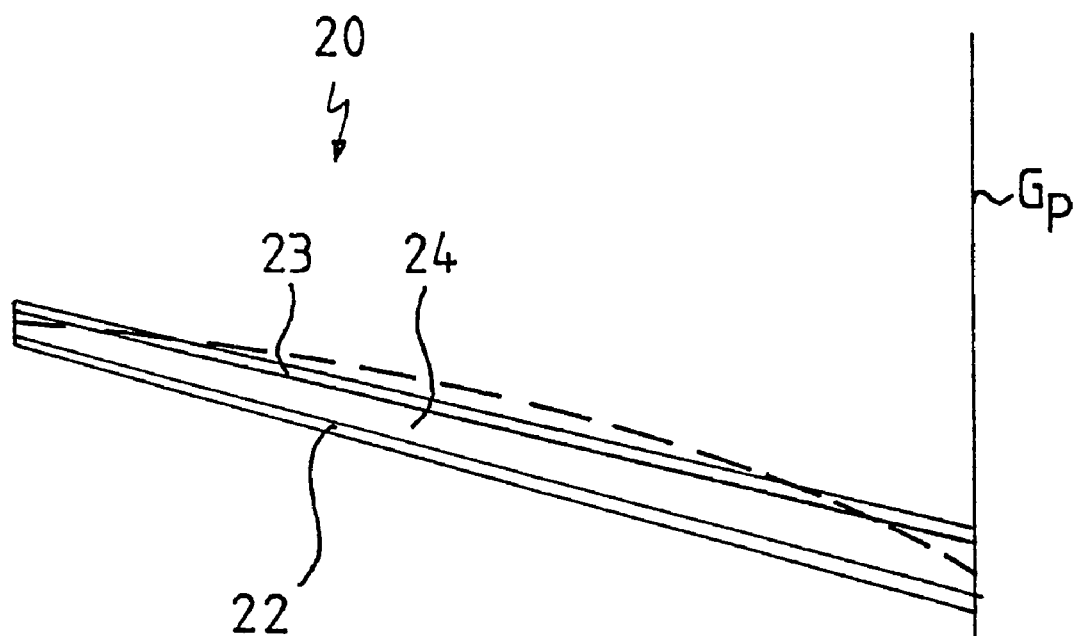
FIG. 4 shows a schematic lateral view of a linear locking element.

In FIG. 3, a partial view of an embodiment of a locking element 20' of a joint socket according to the present invention is shown in a view from the pole. The shown locking element 20' comprises a knock-in web 21 which has a particularly preferred geometry. A distal, or equatorial, end of the knock-in web 21 is further away the socket base surface $G_p$ while a proximal, or pole-side, end of the knock-in web 21 is closer to the socket base surface $G_P$. Knock-in web 21 is angled with respect to socket axis $A_p$. The gradient, with respect to socket axis $A_p$, increases continuously from the distal, or equatorial, end to the proximal, or pole-side, end of the web 21. When the inventive joint socket is advanced into a prepared cavity, the angular deviation of knock-in web 21 with respect to socket axis $A_p$ allows the joint socket to twist about a polar axis. The angular deviation, or gradient, of knock-in web 21 is defined by the angle measured between socket base surface $G_p$ and knock-in web 21. FIG. 4 shows a lateral view of a joint socket showing a more simply designed web 21 which assumes a linear course with a constant gradient. The contour of the web according to FIG. 3 is shown dashed in FIG. 4 in order to emphasize the increasing gradient of the knock-in web 21 of FIG. 3. An angle of twist is defined by an angle measured between socket axis $A_p$ and knock-in web 21. In the embodiments shown in FIGS. 3 and 4, both webs have a gradient of 75° with respect to the socket base surface $G_p$, which corresponds to a twist angle of 15°. In other embodiments, the gradient of the knock-in webs 21 from the distal end of the web to the proximal end of the web 21 may be between 85° to 60°, preferably 80° to 70°, and most preferably 75° with respect to the socket base surface $G_p$. The twist angle is accordingly between 5° to 30°, preferably 10° to 20°, and most preferably 15°.

The curvature, or the increasing gradient, of the web according to FIG. 3 with respect to the base surface leads to the fact that the socket shell, after knocking into the hipbone, is jammed and locked so that a rotating-out counter to the knock-in direction is effectively prevented. The locking elements 20 thus effectively safeguard the implant against i) axial tension forces, ii) radial torsion forces, as well as iii) a combination of both types of forces.

FIG. 3 additionally shows that the width of the web 21 preferably reduces from the web base on the superficies 11 over the whole height of the web. The preferred embodiment of the web 21 shown in FIG. 3 is trapezoidal in cross section and is provided with converging web flanks 22, 23, which enclose an angle γ of 15° to 21°, preferably 18°. The web flanks may also be formed parallel to one another, however the knock-in has been shown to be simpler with the illustrated trapezoidal webs.

As shown in FIG. 3, independent of the size of the joint sockets, the height of the web $H_S$, $H_{S'}$ is between 0.5 and 4 mm, preferably between 1.8 and 2.6 mm. These magnitudes have been shown to be advantageous in view of the physiological properties of the bone into which the webs are knocked.

Figure 5A:
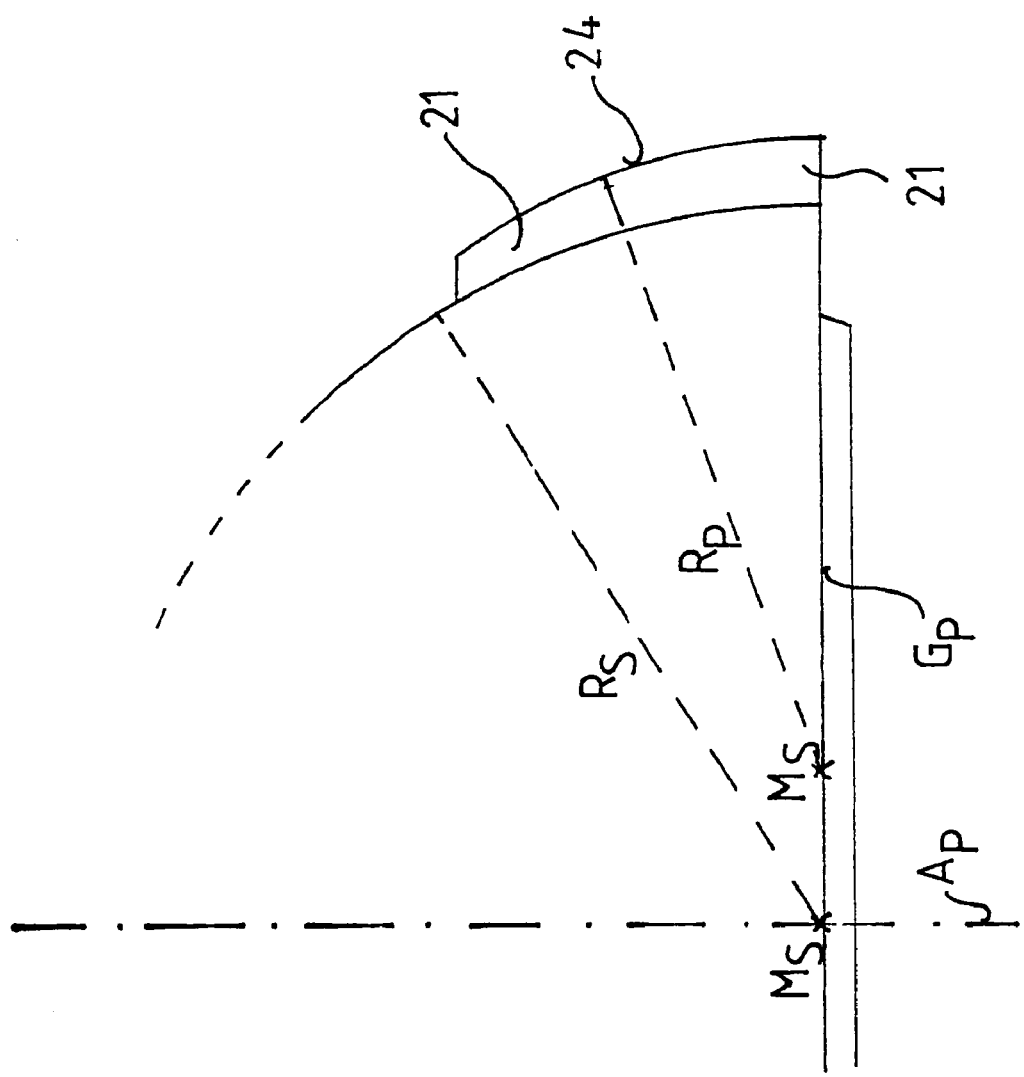
FIG. 5a shows a side view of a distal superficies region of a spherical socket with a locking element as shown in FIG. 3.

As shown in FIG. 3, the width $B_S$ as well as the height $H_S$ of the web 21 reduces from the distal, or equatorial, end to the proximal, or pole-side, end. A lateral view of the web of FIG. 3 is shown in FIG. 5a. As shown in FIG. 5a, a cutting surface 24 of the knock-in web 21 follows a circular arc with a radius $R_p$ which is smaller than the superficies radius $R_S$ of the corresponding ball layer so that the extension of the cutting surface 24 converges with the superficies 11. The web height $H_S$ at the distal or equatorial end is between 1 and 4 mm, preferably 2.4 and 2.8 mm. At the proximal end, the web height $H_S$ is between 0.5 and 3 mm, preferably 1.5 to 1.8 mm. The height thus continuously reduces from the distal to the proximal or pole-side end of the web 21.

Figure 5B:
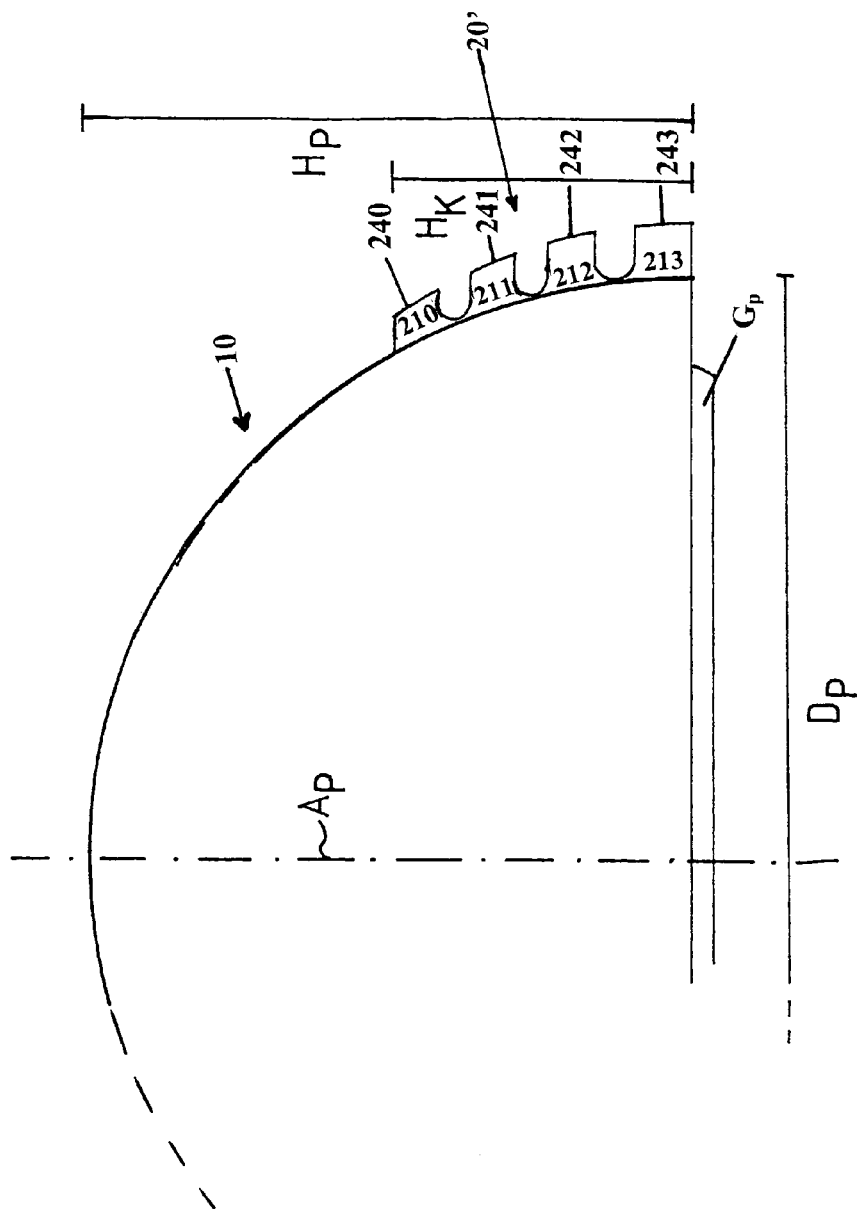
FIG. 5b shows a side view of a distal superficies region of a spherical socket with another embodiment of the locking element.

As shown in FIG. 5b, the web 21 proceeding from the distal socket base surface $G_P$ extends only roughly up to half the socket height in the direction of the pole. If the socket were lopped at the proximal web end then a distal spherical layer of the base body 10 would remain, whose height $H_K$ would then correspond to between 20 to 30%, preferably 24 to 26% of the socket diameter $D_P$. Since the socket needs to be knocked into a pre-milled spherical bed in the bone, the cutting and jamming effect of the knock-in webs 21 reduces with an increasing distance to the socket base surface $G_P$. Web portions in the pole region would no longer contribute significantly to the securing of the implant according to the invention, but would only be further axially squeezed into the bone, similar to the known spikes.

The configuration of a socket for conical implants is different from that of a spherical socket. For a conically-shaped socket, the locking elements may advantageously extend over approximately the entire height of the socket.

Figure 5C:
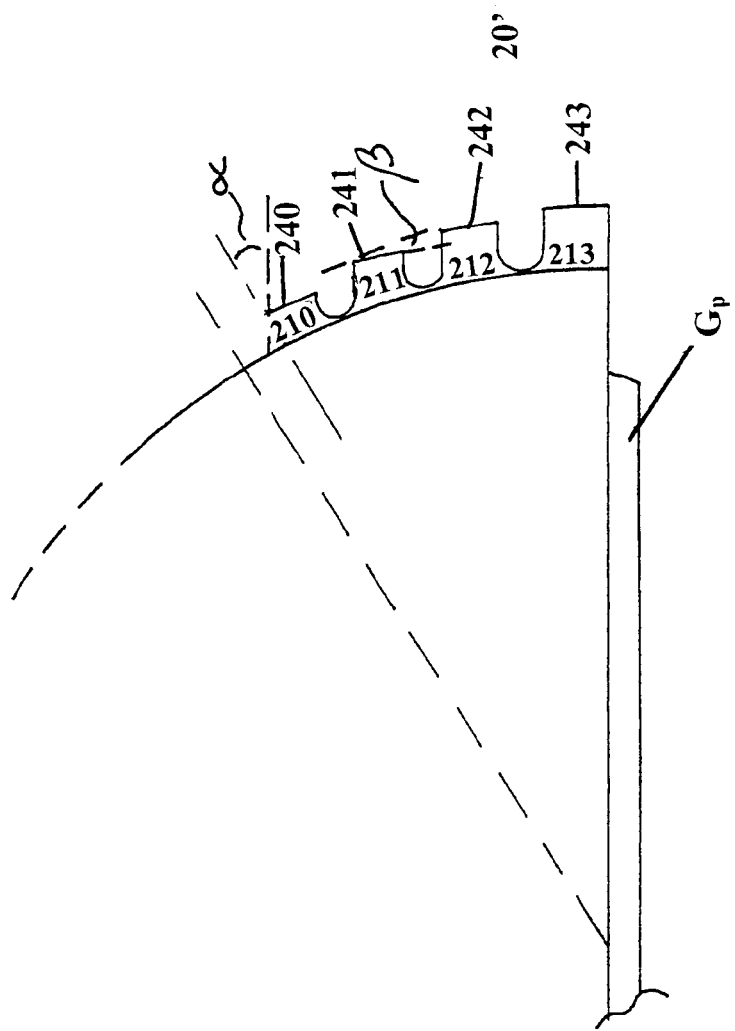
FIG. 5c shows a side view of the distal superficies region of a spherical socket with a further embodiment of the locking element.

In the embodiments shown in FIGS. 2, 5b and 5c, the joint socket is provided with locking elements 20 that do not comprise continuous webs 21, but rather, comprise interrupted webs 21 wherein cutting and clamping teeth 210, 211, 212, 213 are formed. The teeth simplify the knock-in of the implants and provide additional surface area for a later intergrowth of bone cells on the webs. A further advantage of the teeth is that the distal rear sides of the teeth lock the implant particularly effectively in a bone upon tensile loading.

An improved cutting effect on knocking in is achieved in that the upper cutting surfaces 240, 241, 242 of the proximal teeth 210, 211, 212 have a clearance. The cutting surfaces 240, 241, 242 are thus slanted about a clearance angle $\beta$ with respect to the cutting circular arc with the radius $R_S$, so that an actual cutting edge 251 arises at the respective end face 250 of a tooth 211.

As shown in FIGS. 3 and 5c, in addition to the clearance of the proximal teeth 210, 211, 212, a further measure is provided for simplifying the knocking in. The respective first proximal cutting or jamming tooth 210 of a locking element 20' comprises a front cutting surface 214 which is positioned at an effective cutting angle $\alpha$ with respect to the socket base surface $G_P$. The front cutting surface 214 thus does not lie parallel to the socket base surface $G_P$, but rather is set steeper and preferably defines a plane which is approximately perpendicular to the superficies 11.

In the previously described embodiments of the present invention, the locking elements 20 or 20' were formed as one piece with the base body or with the shell 10. In a further embodiment which is not shown in the figures, the locking elements 20 may be detachably fastened to the shell 10. In addition, the knock-in webs 21 described above are positioned on a base or carrier element, which may be introduced into a corresponding groove in the socket shell 10 in an exact fit manner. If the locking elements 20 are manufactured separately from the base body 10, one may utilize various material combinations for the shell and the locking elements. The locking elements 20 are preferably applied and secured in the base body 10 before knocking into the corresponding grooves in the base body 10. It is however possible to first knock in the socket before securing it with the separate locking elements 20.

We claim:

1. A socket, comprising:
   (a) a base body having a superficies, the superficies being essentially rotationally symmetrical relative to a vertical axis of the socket; and
   (b) at least two locking elements positioned on an outer surface of the base body, wherein each of the locking elements comprises at least one knock-in web, the knock-in web having a gradient from a distal web end to a proximal web end of at least 85° to 60° with respect to a base surface of the socket lying perpendicular to the vertical axis of the socket.

2. The socket according to claim 1, wherein the shape of the superficies is selected from the group consisting of: spherical, ellipsoidal, and conical.

3. The socket according to claim 1, wherein the at least two locking elements are distributed symmetrically over the outer surface of the socket.

4. The socket according to claim 1, wherein the at least two locking elements are arranged uniformly distanced to one another.

5. The socket according to claim 1, wherein the gradient increases from a distal end towards a proximal end of the web, with respect to the socket base surface lying perpendicular to the socket axis.

6. The socket according to claim 1, wherein a cutting radius of each of the at least two locking elements is smaller than a radius of the superficies of the base body, whereby an extension of a cutting surface converges with the superficies.

7. The socket according to claim 1, wherein the at least one web extends over a distal region of the superficies of the base body, and wherein the height of the region correspond to between 20 to 30% of the socket diameter.

8. The socket according to claim 1, wherein the height of each of knock-in web is between 0.5 and 4 mm.

9. The socket according to claim 8, wherein the height of the knock-in web reduces continuously from a distal end towards a proximal end of the web, and wherein the height of the web at the distal end is between 1 and 4 mm, and the height of the web at the proximal end is between 0.5 and 3 mm.

10. The socket according to claim 1, wherein the width of the at least one web in its cross section reduces from the base of the web on the superficies over the entire height of the web.

11. The socket according to claim 10, wherein the at least one web is trapezoidal in cross section and comprises at least two web flanks, which converge to one another and enclose an angle between 15° to 21°.

12. The socket according to claim 1, wherein the width and the height of each of the knock-in web reduces from a distal end towards a proximal end.

13. The socket according to claim 1, wherein the at least one web comprises at least two cutting and jamming teeth.

14. The socket according to claim 13, wherein the at least two teeth each comprise an upper cutting surface which is arranged at least partly at a clearance angle with respect to the radius of a cutting circular arc.

15. The socket according to claim 13, wherein a proximal cutting and jamming tooth further comprises a front cutting surface which is arranged at an effective cutting angle with respect to the base surface of the socket.

16. The socket according to claim 1, wherein the at least two locking elements are integrally formed with the base body.

17. The socket according to claim 1, wherein the at least two locking elements may be detachably fastenable to the base body.

18. The socket according to claim 1, wherein the at least one knock-in web defines a gradient of 80° to 70° from a distal web end to a proximal web end with respect to the base surface, corresponding to an angle of twist of 10° to 20°.

19. The socket according to claim 1, wherein the knock-in web further defines an angle of twist with respect to the axis of socket of at least 5° to 30°.

20. The socket according to claim 1, wherein the socket is selected from a group consisting of: joint socket for an artificial hip joint, press-fit socket for an artificial hip joint, and joint prosthesis for knocking into a bone.

* * * * *